(12) United States Patent
Lihl et al.

(10) Patent No.: US 8,585,985 B2
(45) Date of Patent: Nov. 19, 2013

(54) STAINING APPARATUS FOR SAMPLE SECTIONS

(75) Inventors: Reinhard Lihl, Vienna (AT); Heinz Plank, Wr. Neudorf (AD); Siegfried Tanki, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 1072 days.

(21) Appl. No.: 12/176,820

(22) Filed: Jul. 21, 2008

(65) Prior Publication Data
US 2009/0028757 A1    Jan. 29, 2009

(30) Foreign Application Priority Data
Jul. 27, 2007   (DE) .................... 20 2007 010 593 U

(51) Int. Cl.
*A61B 10/00*   (2006.01)
(52) U.S. Cl.
USPC .............. 422/536; 422/65; 422/67; 422/68.1; 422/537; 422/538; 436/180

(58) Field of Classification Search
USPC .............. 422/63–67, 68.1, 536–538; 436/180
See application file for complete search history.

(56) References Cited

U.S. PATENT DOCUMENTS

| | | | | |
|---|---|---|---|---|
| 5,559,032 A | * | 9/1996 | Pomeroy et al. ........... | 435/289.1 |
| 5,674,052 A | * | 10/1997 | Berra ............................. | 417/53 |
| 2002/0146816 A1 | * | 10/2002 | Vellinger et al. ........... | 435/289.1 |

* cited by examiner

*Primary Examiner* — Jyoti Nagpaul
(74) *Attorney, Agent, or Firm* — Schlee IP International, P.C.; Alexander R. Schlee

(57) ABSTRACT

An apparatus for staining sample sections, comprising: a chamber that is adapted for fastening sample sections therein; and a pump that is adapted for pumping liquids through the chamber. The chamber has an inlet and an outlet. The inlet can be connected to at least one reservoir of a staining liquid via inlet lines that are controllable by valves. The inlet lines are formed at least in the region of the associated valves by means of elastic hose lines, and the valves are formed as hose pinch valves. This apparatus minimizes or eliminates contaminations arising from staining processes for thin sections that are in particular prepared for examination in an electron microscope.

12 Claims, 3 Drawing Sheets

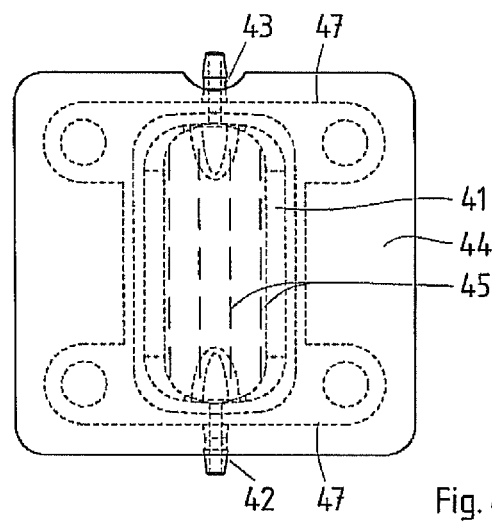
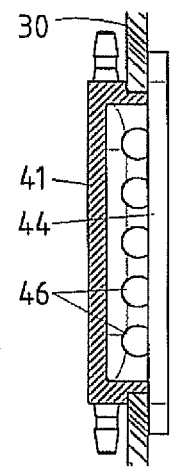
Fig. 4
Fig. 5
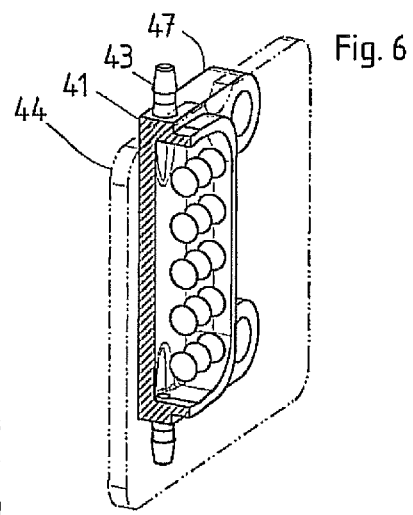
Fig. 6
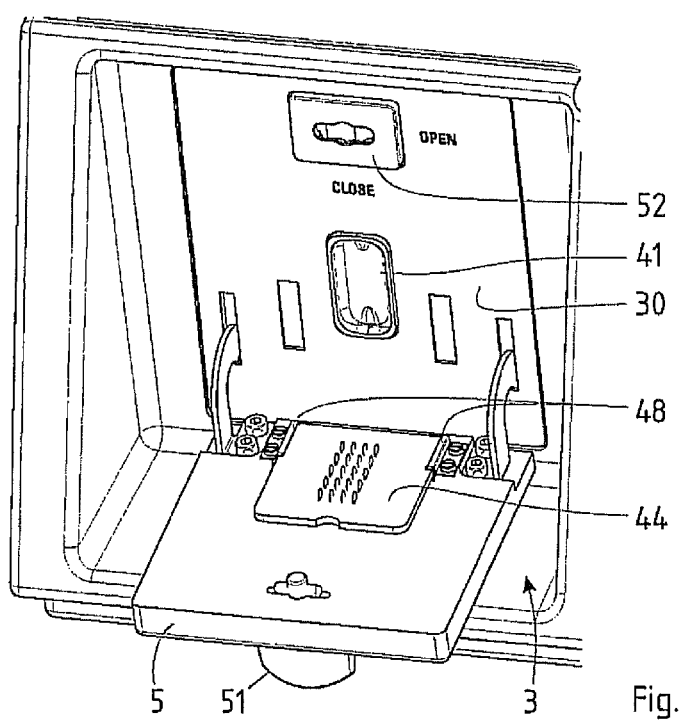
Fig. 7

STAINING APPARATUS FOR SAMPLE SECTIONS

This application claims the priority of the German patent application DE 20 2007 010 593.2 having a filing date of Jul. 27, 2007, the entire content of which is herewith incorporated by reference.

BACKGROUND OF THE INVENTION

The invention relates to an apparatus for staining sample sections, in particular ultrathin sections, having a chamber, in which sample sections can be fastened, and having a pump for pumping liquids through the chamber, the chamber having an inlet and an outlet, the inlet being able to be connected to at least one reservoir of a staining liquid via inlet lines which can be controlled by valves.

Staining apparatuses of this type are well known. The thin sections which are to be treated in the staining apparatus are prepared in particular for examination in an electron microscope. A number of sample sections, e.g. up to 25, are processed in an air-tight sealed chamber with a programmable sequence of staining solutions which are channelled through the chamber, to be precise. The staining liquids are—usually interspersed by rinsing steps using water—pumped into the chamber in which the thin sections are located and held by so-called grids as carriers.

A staining method of particular importance is so-called double staining. The staining solutions used in this case are uranyl acetate and lead citrate solutions, which are problematic on account of their susceptibility to vibrations and contact with unwanted surrounding substances, but also due to their toxicity. Lead citrate in particular forms insoluble precipitates with carbon dioxide particularly easily, which are deposited on the sections and/or in the lines. If washing programs are not carried out reliably, this results in failure of the apparatus (contamination of the hoses, valves and the pump).

A program sequence of double staining for example comprises the following steps: filling the chamber with water, replacing the water with the first staining liquid ("Stain 1"=uranyl acetate solution), replacing the liquid with water for rinsing, replacing the water with the second staining liquid ("Stain 2"=lead citrate solution), replacing the liquid with water. However, individual program steps can be changed.

Manual staining is an alternative to automated staining. In this case, a number of drops of the required liquids are applied next to each other on a clean base (e.g. Parafilm), namely in each case the uranyl acetate solution, water, the lead citrate solution and water again. Each grid (with the section on the underside) is applied in succession onto the drops with the aid of tweezers. Although this method uses small quantities of the staining liquids, it is very error prone—in particular if a large number of sections are to be treated—and the user easily comes into contact with the toxic solution substances.

A staining apparatus for the automated implementation of double staining of thin sections is the applicant's "µM STAIN" apparatus. In the case of this apparatus, conventional magnetic valves with Teflon seats are used to control the liquid supply. The liquids are pumped through Teflon hoses, which are distinguished by a high resistance but are rather brittle, by means of a ceramic or a membrane pump. The treatment of the sensitive staining liquids is still problematic in the case of this apparatus. That is to say, it has been shown that the line-pump systems are particularly sensitive to precipitates, which can lead to blockages of the pump, malfunctions of the valves or obstructions in the hose lines. Furthermore, the ceramic pumps in particular have been found to be susceptible to the transported chemical substances. The valves and the pump itself usually cannot be cleaned sufficiently in the case of servicing and thus have to be replaced by new ones, which leads to very high service costs.

SUMMARY OF THE INVENTION

It is thus an object of the invention to avoid contaminations which could arise due to the staining procedure as far as possible. It is a further object to ease decontamination if contaminations do occur. This holds both for the lines themselves and also the pump, since in the case of current apparatuses there is often a decrease in the power of the pump due to deposits in the pump (e.g. on the membrane).

This object is achieved by a staining apparatus of the type mentioned initially, in which, according to the invention, at least in the region of the associated valves, the inlet lines are formed by means of elastic hose lines, with the valves being formed as hose pinch valves.

The set object is achieved in an elegant manner by means of the inventive solution. The use of elastic hose lines and hose pinch vales considerably reduces the number of components and surfaces which come into contact with the sensitive solutions. In addition, the use of elastic hoses contributes to the liquid flow being guided steadily, which is likewise advantageous due to the sensitivity of the staining liquid to impacts.

A further advantage of the invention lies in the simplification of servicing and repairs, since only the affected hose parts (or hose connectors connecting hose sections, which are likewise consumable articles) have to be replaced for decontamination, whereas the valve mechanics themselves are not affected. In this sense, it is particularly advantageous if the hose lines and the associated connection parts are designed as exchangeable consumable parts.

In terms of a further improvement in the ease of servicing, it is additionally advantageous if the pump is formed as a hose pump.

In order to minimize the effects of the pumping system on the liquids pumped through it, the pump can advantageously be arranged downstream of the chamber.

Furthermore, to simplify the line system, the lines belonging to the outlet can also be formed as hose lines.

In addition, it is advantageous if a washing program can be started after completion of a sequence of staining cycles in order to remove remains of the staining solutions, which could lead to contaminations if they remained for long periods of time, from the hoses. Advantageously, this washing program is built into the sequence control, so that it cannot be circumvented by the user.

For this purpose, it is expedient if, in addition to at least one inlet line for staining liquid(s), an additional inlet line for rinsing water which can be connected to a water container and rinsing lines which draw from the rinsing-water inlet line to the start of the at least one staining-liquid inlet line and discharge into it there in each case via a valve are provided. The position of the valve can be monitored by control electronics, e.g. to the effect that the user (manually) sets the correct position; the control would await the setting of the correct position and stop the staining program until then. The control electronics can additionally be set so that a rinsing program for the inlet lines of the staining liquids is to be carried out after the staining program has been completed and cannot be circumvented by the user.

A further improvement in the handling and consumption of the liquids results from an improved design of the chamber geometry. In addition to a reduction is size of the chamber cavity itself, it is advantageous if the inlet of the chamber is arranged at a location lying at the bottom and the outlet is arranged at a location lying at the top of the chamber cavity, and if the chamber cavity has an elongated design such that the vertical extent of the chamber cavity between the inlet and outlet is longer than its lateral width.

BRIEF DESCRIPTION OF THE DRAWINGS

The invention along with further advantages is described below on the basis of an exemplary embodiment, which does not restrict the invention, relating to an apparatus for automated implementation of double staining of thin sections. It is illustrated in the attached drawings, in which:

FIG. 4 shows a front view of the chamber of the staining apparatus;

FIGS. 5 and 6 show the chamber according to FIG. 4 with inserted section grids in partial sectional views, namely from the side (FIG. 5) and in an oblique view (FIG. 6);

FIG. 7 shows the chamber mounted in the staining apparatus in the opened state.

DETAILED DESCRIPTION OF THE DRAWINGS

Figure 1:
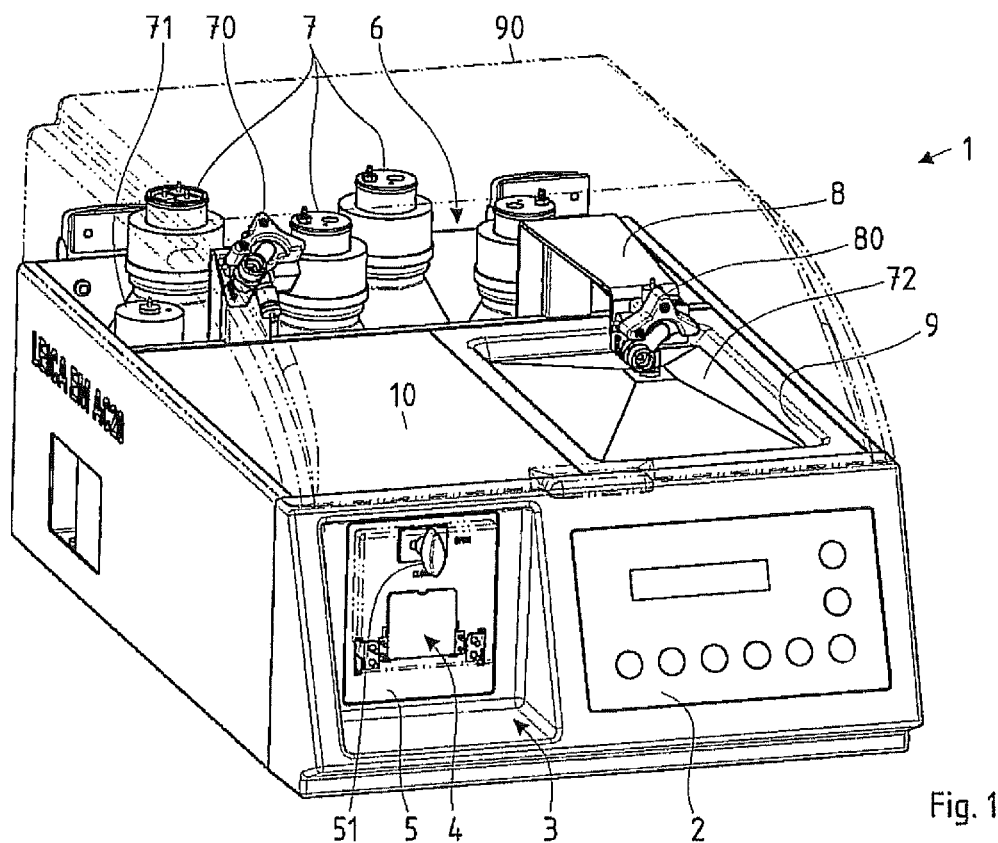
FIG. 1 shows an oblique view of the staining apparatus of the exemplary embodiment.

FIG. 1 shows a staining apparatus 1 according to a preferred exemplary embodiment of the invention, which is a refinement of the known apparatus "EM STAIN" of the applicant. The apparatus is described in the following to the extent that is required to understand the invention. Additional details of the operation of staining equipment and, in particular, handling of the liquids and the liquid containers correspond to those of the "EM STAIN" apparatus.

A chamber niche 3, in which the staining chamber 4 (chamber for short) is housed under a cover plate 5, is located on the front side of the apparatus 1 next to an operating panel 2, which comprises a display and a number of operating buttons. The cover plate 5 can be fixed by means of a rotary lever 51 located above the chamber 4. A compartment 6 with a number of liquid containers 7 is located in the back part of the apparatus. Some of the containers 7 contain different liquids required for the staining process and some contain used liquids. Advantageously, the containers are glass bottles, from which hose lines—which are not shown in FIG. 1 on grounds of clarity—are drawn into the apparatus. Deviating from the "EM STAIN" apparatus, the container 71 for the first staining liquid (uranyl acetate) is also implemented as one of the container bottles 7. On the other hand, the second staining liquid (lead citrate) is stored in its own, air-tightly sealed bag 72 ("stain bag"), for which a bowl 9 is provided on the right side of the top side of the apparatus. In the middle of its top side, the bag 72 has a connecting piece with a connection device 80, by means of which the staining liquid can be removed and which is described in more detail below. An arm 8 mounted above the bowl holds the connecting piece in its position and serves as a holder for the hose line for the staining liquid (not shown) and electronic components for monitoring the tap 80. A mains adaptor and control electronics 19 of the apparatus 1 are located below the bowl 9. A removable cover plate 10 is located to the left of the bowl 9, which allows the user access to a line system (FIG. 2), including pump and valves, located in the space behind the chamber niche 3. A transparent, removable cover 90 (illustrated by the dash-dotted lines in FIG. 1) protects the containers 7 and the arm 8 during the staining procedure; it is only opened for servicing, including refilling the liquids or changing the containers, and repairs, as well as to actuate the rinsing taps 21 in the case of the rinsing procedure.

Figure 2:
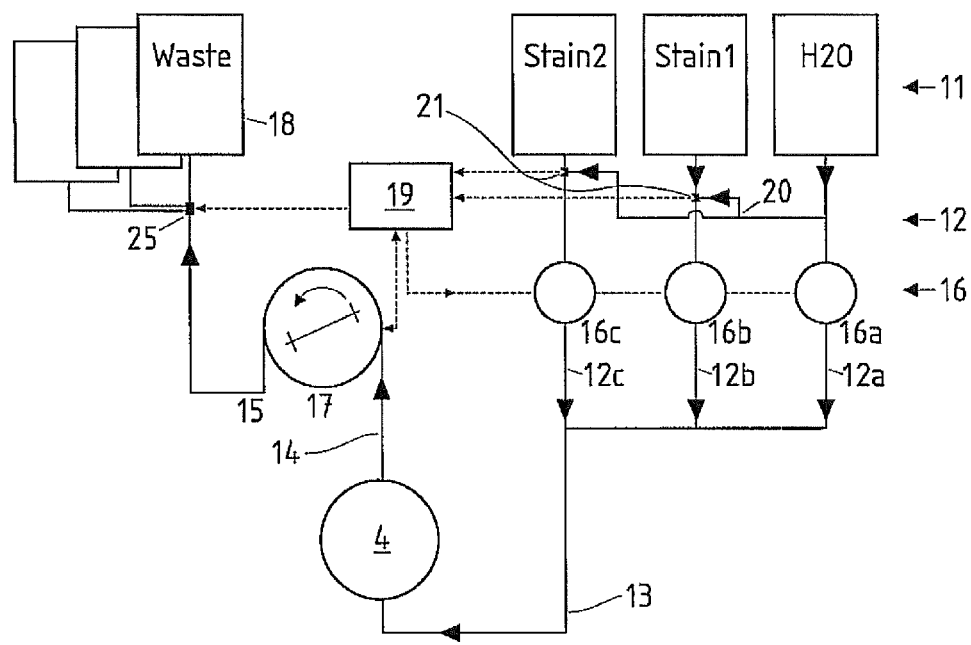
FIG. 2 shows a schematic of the line system of the staining apparatus.

FIG. 2 shows a schematic of the line system used in the staining apparatus according to FIG. 1. The main component of the line system is naturally the chamber 4. In the operating state, the chamber 4 is closed in an air-tight and liquid-tight manner, with the exception of an inlet and an outlet (FIG. 4). The liquids fed into the system which are required for the staining procedure are contained in containers 11, the contents of which are additionally indicated in FIG. 2 by means of the references "Stain1", "Stain2" and "H2O".

Inlet lines 12, 13, which are controlled by pinch valves 16, feed the liquids of the containers 11 to the chamber 4. Each of the liquids fed is assigned to one respective inlet line 12a, 12b, 12c, which is led through an associated valve 16a, 16b, 16c and finally discharges into the chamber inlet line 13. A pump 17 designed as a hose pump is provided on the outlet side (i.e. downstream) of the chamber. The outlet of the pump leads to one or more waste-water containers 18 ("Waste") via outlet lines 15.

The pump 17 pumps the liquids through the chamber 4 by suction out of the containers 11. It is an important detail of the arrangement that the pump 17 is arranged downstream of the chamber in order to keep the line circuit as simple as possible in front of the chamber, so as to minimize sources of possible contamination.

Furthermore, in the apparatus 1 the inlet lines 12b, 12c assigned to the staining solutions ("Stain1", "Stain2") are in each case equipped with an additional rinse inlet 20. The latter is formed for example with the aid of a three-way tap 21 connected to the inlet line. Water is allowed to be fed in through the rinse-inlet, e.g. from the line 12a of the water container or an own rinse water container (not shown), in order to be able to rinse the lines 12b, 12c with water after the end of the program. What is achieved is that no staining liquid, which can lead to contaminations (precipitates) due to the unavoidable diffusion of gasses from the surrounding air, remains in the lines during operating breaks.

Preferably, the rinse-inlet 20 is shifted as close to the start of the respective line 12b, 12c as possible. In the case of the lead citrate container, the tap of the rinse-inlet is advantageously integrated into the nipple of the container, so that the rinse-inlet is effectively arranged immediately downstream of the container.

In place of a combined waste-water container 18, the used liquids can be distributed into different waste containers depending on the pumped liquid by means of further valves 25. Additionally, further valves can be provided in the outlet and inlet lines 13, 14 of the chamber so as to be able to air and empty the chamber after the staining procedure has been completed.

Figure 3:
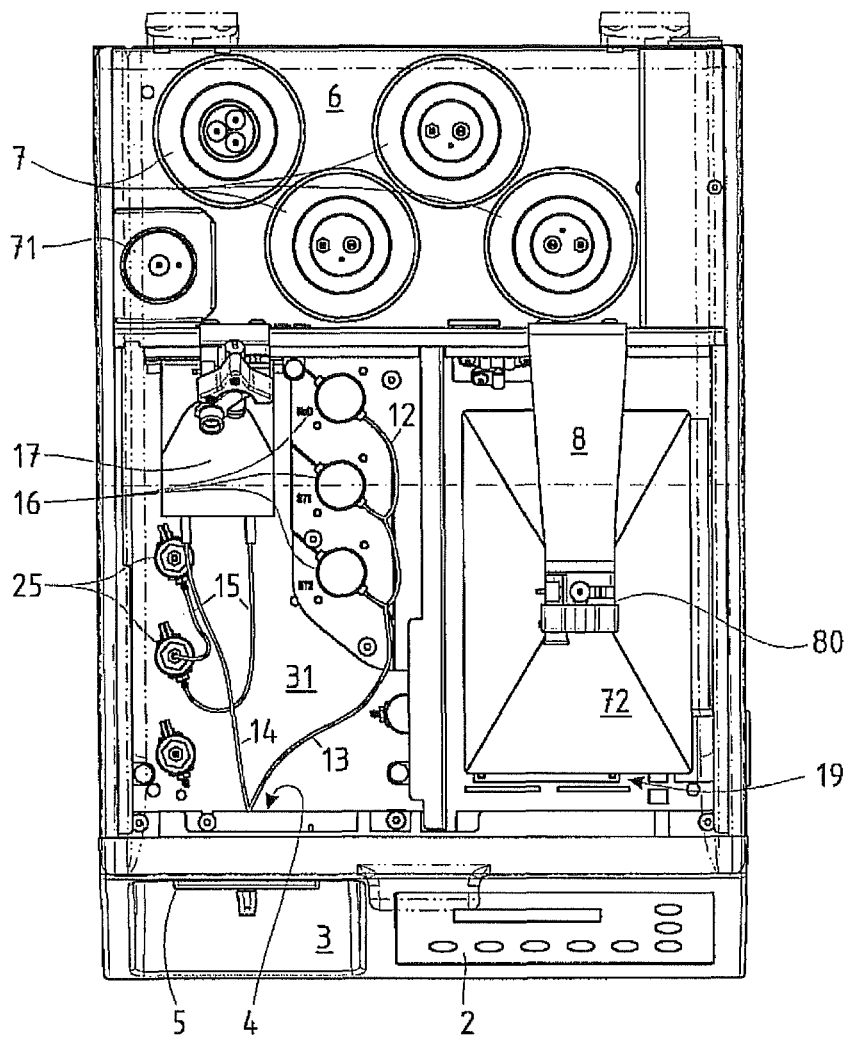
FIG. 3 shows a plan view of the staining apparatus.

FIG. 3 shows a plan view of the apparatus with the cover removed and the cover plate (10 in FIG. 1) opened, so that the valve-pump space 31 lying under the cover plate is visible. The valves 16, the pump 17 and further components of the line system if required are located in it. For reasons of clarity, only some of the hose lines are shown, namely the inlet lines 12 from the valves 16 and the chamber inlet and outlet lines 13, 14, and some of the pump outlet lines 14; the layout of the other lines results directly from the line plan of FIG. 2. All lines of the line system, but at least those in the valve-pump space 31, are preferably formed as silicon hoses; in addition other suitable elastic materials are also possible, such as e.g. neoprene, which allows a hose to be clamped shut without being irreversibly deformed or even breaking. These lines and associated line connectors, such as e.g. the Y-pieces of the inlet lines 12, are consumable parts, which can be exchanged with little effort.

As already mentioned, a space for the apparatus electronics 19, including the mains adaptor and controls, is located next to the space 31 and partly covered by the stain bag 72. As already mentioned, all hose lines in the apparatus 1 are designed in an accessible way, in order to enable simple exchange of the hoses.

The control of the inflow of the liquids through the inlet lines 12 is carried out by means of pinch valves 16, with whose help the inlet lines 12 can be individually closed or opened. The pinch valves are preferably closed in the current-free state and can be formed for example as pinch solenoid valves from the Sirai company (Italy) e.g. of the type S105. Pinch valves work on the principle of a flexible hose, which is led through the valve, being pinched from the outside in order to close it, and the hose cavity thus being compressed. A typical form of a pinch valve comprises a hose clamp, which is e.g. held by an adjustment spring and is acted on by an electromagnetic actuator, so that it pinches or frees the through flow of the pumped medium. The flow can go in both directions without turbulence or stagnation points occurring in this case in the hose.

The use of pinch valves within the scope of the invention leads to two substantial advantages: on the one hand a steady flow without deflection in the valve is possible in the opened state—there are no valve parts protruding into the cavity (risk of contamination). On the other hand, should contamination occur, the hose can be replaced in a simple manner, the hose only having to be pulled through the (kept open) valve; the valve itself need not be replaced.

For corresponding reasons, the use of a hose pump, also referred to as a hose pinch pump or a peristaltic pump, is preferred for the pump 17. This type of pump is almost completely insensitive to contaminations in the hose cavity and does not provide additional surfaces (e.g. a membrane or a slider) on which contaminations could be deposited. By way of example, in the embodiment shown, peristaltic pumps of the type Thomas SR25-S300 of the Gardner Denver Thomas GmbH company of Puchheim (Germany) are used, which are powered by a stepper motor. The use of a hose pump in place of a membrane pump likewise has the advantage of an easy hose exchange if problems should occur, in particular due to hose contaminations. Furthermore, a hose pump has a very precise delivery rate. Furthermore, the hose pump is insensitive to the type of liquid pumped, since the movable parts do not come into contact with the liquid; this includes the case in which air is transported, e.g. in the final emptying of the hose lines.

It is pointed out that, due to the use of a hose pump 17, the lines of the pump inlet and outlet are formed as one continuous piece of hose which is led through the equipment of the hose pump in a known manner.

Figure 8:
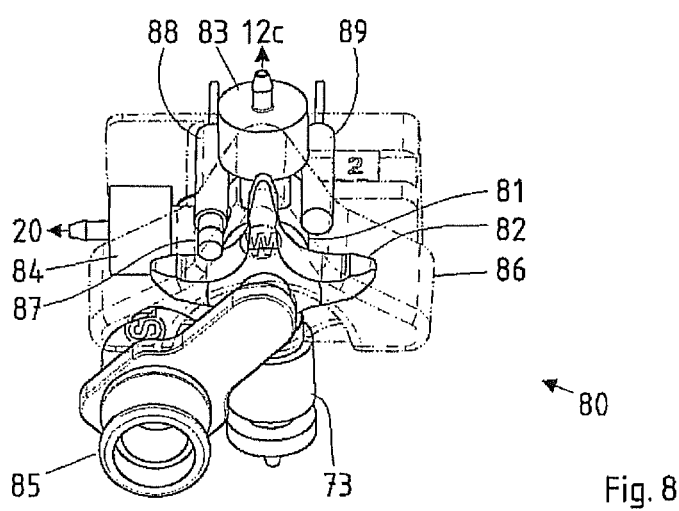
FIG. 8 shows the connection device of a staining liquid container.

Referring back to FIG. 2, in a preferred embodiment of the invention, the taps 21, 81 of the rinse-inlets 20 are to be operated by hand; however the position of the taps is monitored by magnetic pick-ups and controlled by the control 19. This is shown in FIG. 8 by the example of the connection device 80 for the stain bag 72 of the second staining liquid. The connection device 70 (FIG. 1) belonging to the container 71 is formed in a corresponding manner as a removable top of the container bottle.

As can be seen in FIG. 8, a tap 81 which is implemented as a manually operable three-way valve is seated on the connecting piece 73 of the bag. A handle piece 82 in the form of an upside-down T serves to actuate the valve. A connection 83 for the inlet line 12c is made to extend upwards from the tap 81 and a connection 84 for the rinsing line 20 is made to extend to the side (to the left in FIG. 8). By way of example, the two lines are connected by Luer lock connections to the connections 83, 84 of the tap. A holding piece 85 penetrates the tap 81 and the handle piece along its rotational axis, and connects these towards the back to the arm 8.

In the position shown in FIG. 8, the tap is in the rinsing position, in which the staining liquid is locked in the bag and rinsing water can flow into the line 12c from the rinsing line; by turning the handle piece 82 (90° clockwise in FIG. 8), the process position is achieved, wherein the staining liquid can be extracted via the line 12c and the rinsing line is locked. So that the position of the tap 81 can be controlled by the control electronics 19, a plastic piece 86 (illustrated dash-dotted for reasons of clarity) is attached to the handle piece 82 with the aid of the holding piece 85, the plastic piece in turn holding an actuating magnet 87; in the embodiment shown, the actuating magnet comprises two magnet pieces in order to achieve a better magnetic field configuration. Sensors 88, 89 are provided on both sides of the connection 83, e.g. reed sensors. In the rinsing position (as shown in FIG. 8), the magnet 87 is in the proximity of the first sensor 88, however, in the process position it is opposite the second sensor 89. The sensors are connected to the control electronics 19 via electric connection lines.

Referring back to FIG. 2, at the beginning of the rinsing program, the user is prompted to place the taps 21 into the rinsing position and the rinsing program is not continued until the taps have been correspondingly set. If the user should (wrongly) displace the taps during the rinsing, this can likewise be detected, and the rinsing program is interrupted—whilst issuing a corresponding error message—until the correct tap position has been re-set. Expediently, the control electronics can be programmed such that a rinsing program for the inlet lines of the staining liquids must be carried out after the completion of a staining program, without the user being able to circumvent it. Conversely, the position of the taps of the rinsing inlets are monitored during the staining processes to the effect that they are set to the process position.

FIG. 4 shows a front view of the chamber 4. The chamber cavity is enclosed by a chamber body 41, which surrounds the chamber cavity like a bowl and has an input 42 and output 43. The input 42 and output 43 are expediently designed as connection nipples for hose lines. The chamber body 41 can be mounted in the chamber niche 3 and is composed, e.g. of polycarbonate. The chamber body 41 is supplemented by a removable holding plate 44, which covers the chamber on the front side and seals the cavity formed between the chamber body 41 and plate 44 in an air-tight and liquid-tight manner. The plate 44 comprises a material combining chemical resistance with flexibility (Shore hardness below 60), such as silicone or plasticized PVC, and has a number of notches 45, in which the grids holding the thin sections are held. In the view according to FIG. 4, the chamber body is only visible through the (transparent) plate 44.

FIG. 5 shows a cross section of the chamber and FIG. 6 shows a corresponding perspective illustration. Here, the grids 46 held in the holding plate 44 are also illustrated. From these figures it can also be seen that the chamber volume is configured to be as small as possible.

The chamber body 41 has four continuations 47, with the aid of which the chamber body can be fastened from behind through a corresponding opening in the wall 30 of the chamber niche 3. The plate 44 is attached at the front by means of a clamping apparatus (not shown), which can be actuated by means of a rotary lever 51. In contrast to the chamber body which is permanently mounted and is only replaced for repair purposes, the plate 44 can be removed by the user and can be reinstalled, all the more since the plate 44 serves as carrier for the grids with the thin sections to be processed.

FIG. 7 shows the chamber in an opened position. In it, the rotary lever 51 is unlocked and the covering plate 5 is opened towards the front, as a result of which the holding plate 44 is removed from the chamber body 41. The holding plate 44 is kept in the right position on the covering plate with the aid of fixing elements 48, e.g. clamps. In this position, the grids 46 can be removed and/or inserted, or the holding plate 44 can be removed as a whole and can be reinserted after it has been loaded with grids to be processed. Once the plate 44 has been inserted and the cover plate 5 has been closed by locking the rotary lever 51 in the locking device 52 (cf. FIG. 1), the plate is pressed against the chamber body 41 and thus seals the chamber cavity on the front side. A heating foil can additionally be attached to the rear side of the chamber 41, in order to be able to set increased temperatures for the staining procedure, if required.

The chamber volume is markedly decreased compared to earlier staining apparatuses. As a result of this, the consumption of staining liquids is drastically reduced.

Furthermore, the improved chamber geometry contributes to a decreased liquid consumption. For this purpose, the input and output openings at an opposite locations on the bottom side of the bowl are arranged slightly sunken (see FIG. 6). Additionally, the input 42 (inlet) is located below the output 43. Slow, steady liquid flows result due to this and in combination with the steady pumping action of a hose pump. This is particularly important so that the films and the grids containing them are not damaged. Additionally, the slow liquid flows in combination with the elongated chamber design allows for a better exchange of the liquids to be achieved in the chamber, since a displacement is achieved, and mixing is avoided, by means of the laminar flow. This results in an additional decrease in the liquid consumption and the operational costs (cost of acquiring the staining liquids in particular, and their disposal) are markedly reduced as a consequence. Trials have shown that the amount required to replace one liquid by another (e.g. staining agent/water, or vice versa) is in each case only approximately double the volume of the chamber.

The invention claimed is:

1. Apparatus for staining sample sections, comprising:
   a sealable chamber that is adapted for fastening sample sections therein, the sealable chamber having a chamber inlet and a chamber outlet, the chamber inlet being connected to at least one staining liquid reservoir via chamber inlet lines that are controllable by hose pinch valves; and
   a hose pump that is arranged downstream of the sealable chamber adapted for pumping liquids through the chamber and comprises hose lines extending as chamber outlet lines from the chamber outlet to a hose pump inlet through equipment of the hose pump to a hose pump outlet as one continuous piece of hose; wherein
   the chamber inlet lines are at least in the region of the associated hose pinch valves made of elastic hose lines; and
   the hose lines and connection parts connecting the hose lines are designed as replaceable and expendable parts.

2. Apparatus according to claim 1, wherein, in addition to at least one inlet line for staining liquid(s), an additional inlet line for rinsing water is provided that is connectable to a water container; and at least one rinsing line is provided that draws rinsing liquid from the inlet line for rinsing water into the beginning of the at least one staining-liquid inlet line, and discharges into the at least one staining-liquid inlet line through at least one valve.

3. Apparatus according to claim 2, wherein at least two rinsing lines are provided, each one discharging into the at least one staining-liquid inlet line through at least one valve, respectively.

4. Apparatus according to claim 3, wherein the position of the valve is monitored by control electronics.

5. Apparatus according to claim 4, wherein control electronics are provided that are set so that a rinsing program for the chamber inlet lines of the staining liquids is to be carried out after the staining program has been completed and cannot be circumvented by the user.

6. Apparatus according to claim 3, wherein control electronics are provided that are set so that a rinsing program for the chamber inlet lines of the staining liquids is to be carried out after the staining program has been completed and cannot be circumvented by the user.

7. Apparatus according to claim 2, wherein the position of the valve is monitored by control electronics.

8. Apparatus according to claim 7, wherein control electronics are provided that are set so that a rinsing program for the chamber inlet lines of the staining liquids is to be carried out after the staining program has been completed and cannot be circumvented by the user.

9. Apparatus according to claim 2, wherein control electronics are provided that are set so that a rinsing program for the chamber inlet lines of the staining liquids is to be carried out after the staining program has been completed and cannot be circumvented by the user.

10. Apparatus according to claim 1, wherein the chamber inlet is arranged at a location lying at the bottom and the chamber outlet is arranged at a location lying at the top of the chamber cavity.

11. Apparatus according to claim 10, wherein the vertical extent of the chamber cavity between the chamber inlet and chamber outlet is longer than its lateral width.

12. Apparatus according to claim 1, wherein the sections are ultrathin sections.

\* \* \* \* \*

UNITED STATES PATENT AND TRADEMARK OFFICE
CERTIFICATE OF CORRECTION

PATENT NO. : 8,585,985 B2  
APPLICATION NO. : 12/176820  
DATED : November 19, 2013  
INVENTOR(S) : Reinhard Lihl, Heinz Plank and Siegfried Tanki Page 1 of 1

It is certified that error appears in the above-identified patent and that said Letters Patent is hereby corrected as shown below:

In the Specification

Column 1, line 57 reads:

double-staining of thin sections is the applicant's "$\mu$M and should read:

double-staining of thin sections is the applicant's "EM

Signed and Sealed this  
Eighteenth Day of February, 2014

Michelle K. Lee  
*Deputy Director of the United States Patent and Trademark Office*